United States Patent [19]

Buning et al.

[11] 4,404,691

[45] Sep. 20, 1983

[54] MODULAR PROSTHESIS ASSEMBLY

[75] Inventors: Onno Buning, Clarina; Peter Lawes, Castletroy, both of Ireland

[73] Assignee: Howmedica International Inc., Clare, Ireland

[21] Appl. No.: 238,013

[22] Filed: Feb. 25, 1981

[30] Foreign Application Priority Data

Mar. 11, 1980 [GB] United Kingdom ................ 8008140

[51] Int. Cl.$^3$ .............................................. A61F 1/03
[52] U.S. Cl. ..................................... 3/1.911; 3/1.913; 128/92 C
[58] Field of Search ....................... 3/1.9, 1.91, 1.911, 3/1.912, 1.913; 128/92 C, 92 CA

[56] References Cited

U.S. PATENT DOCUMENTS

| | | | |
|---|---|---|---|
| 2,682,265 | 6/1954 | Collison | 128/92 CA |
| 2,719,522 | 10/1955 | Hudack | 3/1.913 X |
| 2,765,787 | 10/1956 | Pellet | 128/92 CA |
| 2,785,673 | 3/1957 | Anderson | 128/92 CA |
| 3,064,645 | 11/1962 | Ficat et al. | 128/92 CA |
| 3,102,536 | 9/1963 | Rose et al. | 128/92 CA |
| 3,662,405 | 5/1972 | Bortz et al. | 128/92 C X |
| 3,806,957 | 4/1974 | Shersher | 3/1.913 |
| 4,167,047 | 9/1979 | Grundei et al. | 3/1.91 X |

FOREIGN PATENT DOCUMENTS

| | | | |
|---|---|---|---|
| 2378505 | 8/1978 | France | 3/1.911 |
| 1443470 | 7/1976 | United Kingdom | 3/1.9 |
| 1521679 | 8/1978 | United Kingdom . | |
| 1531487 | 11/1978 | United Kingdom . | |

OTHER PUBLICATIONS

DePuy Advertisement, *Journal of Bone and Joint Surgery,* Sep. 1960, p. 18.
DePuy Hip Prosthesis with Detachable Head", *DePuy Catalog,* 1964, p. 33.
DePuy Advertisement, *Journal of Bone and Joint Surgery,* Jun., 1955, p. 42.

*Primary Examiner*—Clifford D. Crowder
*Attorney, Agent, or Firm*—Diller, Ramik & Wight

[57] ABSTRACT

A modular prosthesis assembly for replacement of at least part of a joint and part of a bone shaft including a mounting component provided with a connection portion and at least two joint components of similar shape but different dimensions and which can be connected alternatively to the mounting component, each of the joint components having an engagement portion and a connection part adapted for connection to the connection portion of the mounting component, the joint components each providing part of a bone shaft and part of a joint which can cooperate with an appropriate part of a natural or artificial joint.

25 Claims, 12 Drawing Figures

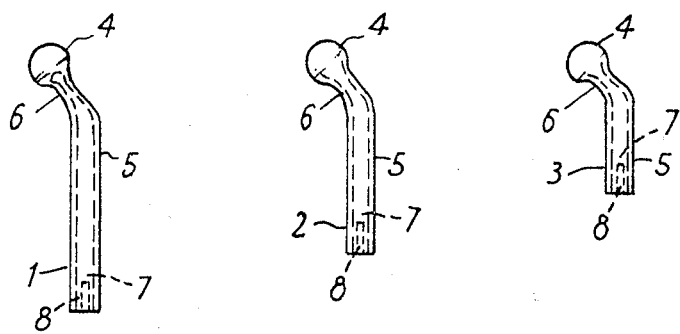
FIG.1
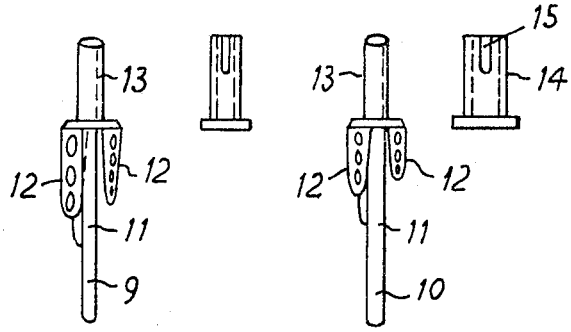
FIG.2
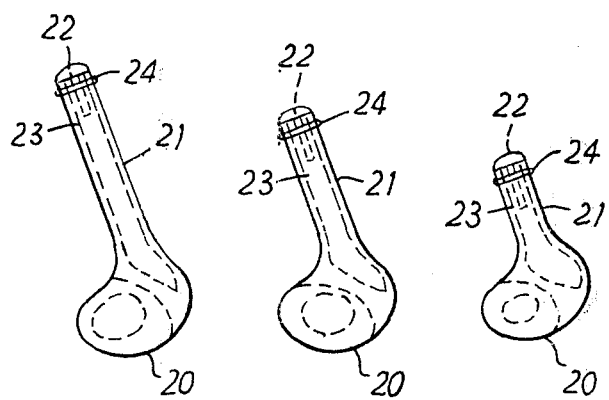

MODULAR PROSTHESIS ASSEMBLY

This invention relates to a modular prosthesis assembly.

It is known to provide prostheses for replacing parts of natural joints for example, to replace the head of the femur in hip joints and to replace the lateral and medial condyles at the lower end of the femur. When parts of the joints are replaced there is sometimes difficulty in selecting an appropriately dimensioned prosthesis component. There are also difficulties if the prosthesis is to be implanted in a growing individual as it is usually necessary to completely remove an originally installed prosthesis and replace it with a larger one as the individual grows.

The present invention is intended to provide a prosthesis assembly using modular components so that an appropriate prosthesis can be made up for an individual quite easily at the time of the operation and, if necessary the operative part of the prosthesis, for example the head of the femur, can be easily removed and replaced by a larger or smaller prosthesis component as is appropriate at some later date.

A further advantage of the invention, when applied in particular one form, is that the components can be interchangeable so that different systems, for example, a hip joint or a knee joint can be constructed from standard parts.

According to the present invention a modular prosthesis assembly for replacement of at least part of a joint comprises a mounting component provided with a connection portion and two or more joint components which are of similar shape but are different sizes and which can be connected alternatively to said mounting component, each joint component having an engagement portion which provides part of a joint and which can co-operate with an appropriate part of a natural joint or a prosthesis replacing it, and a connection part adapted for connection to the connection portion of said mounting component.

It will be appreciated that the assembly can be used to replace parts of the joint carried by a number of bones in the human or animal frame and the present invention is particularly although not exclusively applicable for replacing part of a human femur.

As two or more joint components are provided which are of different sizes this enables the operative part of the joint to be adjusted at the time of the operation as is required, the surgeon being provided with an appropriate selection of sizes.

Preferably two or more mounting components of different sizes are also provided. If, for example, there were three sizes of joint component and two sizes of mounting component then six prosthesis assemblies could be made up all of different dimensions.

In one preferred assembly each of the joint components is in the form of a hip component having a head extending via a neck to said connection part.

With this arrangement the said head and/or said necks of the joint components can be of different sizes.

Alternatively or in combination with the above the joint components can be in the form of femoral knee components each having an engagement portion to co-operate with a natural tibia or a tibia prosthesis component.

Thus, the assembly of parts could be for a replacement hip joint or for replacement of the femoral parts of a knee joint.

Moreover, the assembly may include a tibia component adapted for alternative co-operation with said femoral knee components and having an attachment portion for attachment to a tibia.

With this arrangement two or more tibia components can be provided of different dimensions for alternative use with said femoral knee components.

With these additional components therefore there is also provision for providing a total knee prosthesis.

In one preferred arrangement each of the mounting components has an attachment portion for attachment to a femur of the user so that the prosthesis therefore provides an appropriate end for a femur.

Preferably the arrangement is such that the attachment portion of the mounting component is adapted for attachment to either end of the femur so that a standard mounting component can be provided.

It will therefore be appreciated that a set of parts for dealing with damage to either end of the femur of the patient could comprise a number of mounting components which are of modular design but of different sizes and which can be attached to either end of the femur, two or more hip components of different sizes, two or more femural knee components of different sizes, and two or more tibia components, again of different sizes thus enabling the surgeon to deal with any of the joints connected with the bone concerned.

In the arrangement referred to above the attachment portion of the mounting component is preferably in the form of a stem portion which may be of the Walldius type with three flanges for cementless fixation.

In another, alternative, form of the invention, the mounting components, or each thereof, have connection portions at spaced apart ends, one connection portion being adapted for connection to a joint component in the form of a hip component having a head extending via a neck to said connection part, and the other connection portion being adapted for connection to a joint component in the form of a femural knee component having an engagement portion to co-operate with a natural tibia or a tibia prosthesis component, and including two or more hip components and two or more femural knee components for alternative use.

It will thus be seen that in this arrangement the mounting components provide the main length of the femur itself the hip components and the femural knee component providing the ends.

As two or more mounting components are provided the overall length of the replacement femur can be varied and further variation achieved by use of the alternative joint components.

In a convenient construction the mounting component, or each thereof, can be in the form of a coupling shaft.

Another way of altering the distance between the joint components and at the same time providing a connection between them is to provide means for adjusting the distance between the joint components on the coupling shaft. With this arrangement therefore only one mounting component, in the form of a coupling shaft with means for adjusting the distance between the joint components on it can be provided rather than providing two coupling shafts of different lengths.

Various means can be provided for connecting the joint components to the mounting component but in a preferred construction the connection part of each joint component has a socket in which said connection portion of the co-operating mounting component can be located.

As this socket and the connection part of the mounting component can be made a standard size all the various parts can be interconnected as required.

Preferably the connecting portion has a sleeve mounted on it which is keyed into the socket to prevent relative rotation between the components and this sleeve can be made from a synthetic plastics material.

With this arrangement the sleeve can be arranged to be a press fit onto the connection portion of the mounting component.

The invention can be carried out in many ways and some embodiments will now be described by way of example and with reference to the accompanying drawings in which:

FIG. 1 is a diagrammatic representation of a set of components which can be used together to provide a hip prosthesis;

FIG. 2 is a diagrammatic representation of a set of femural knee components which can be used with the components shown in FIG. 1;

Figure 3:
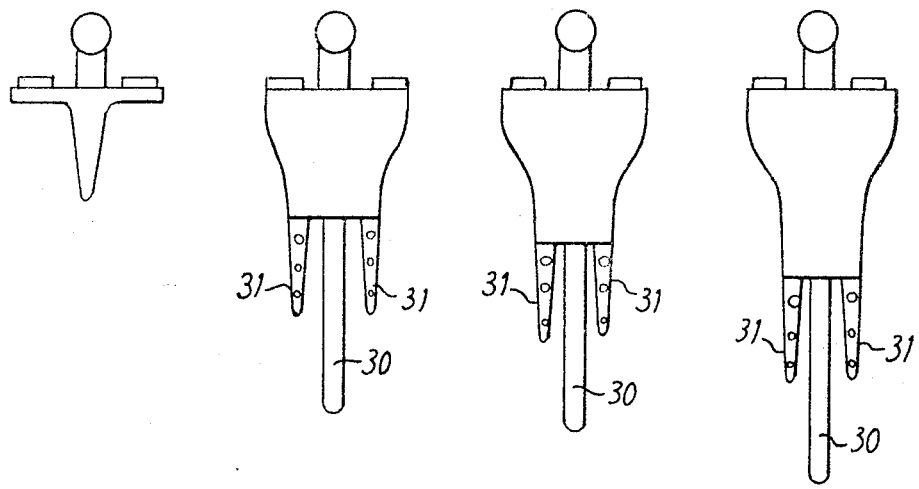
FIG. 3 is a diagrammatic representation of a set of tibial components which can be used with the femural components shown in FIG. 2.

FIG. 1 shows the various components which can be made up to provide a hip prosthesis assembly according to the invention. This prosthesis consists basically of a joint component, in this case a hip component, and a mounting component. In FIG. 1 three hip components are shown indicated by reference numerals 1, 2 and 3. Each hip component comprises a head 4 which is connected to a connection part 5 through a neck 6. In the arrangement being described each of the hip components has a 32 mm head and a standard neck length and can be used as a total hip or with a bicentric floating head. The connection portions are arranged in different lengths so that three hip component sizes are available, 110 mm, 150 mm and 190 mm.

The hip components are hollow so that the support portions, which are cylindrical provide a socket 7 in which is located a key 8.

Figure 10:
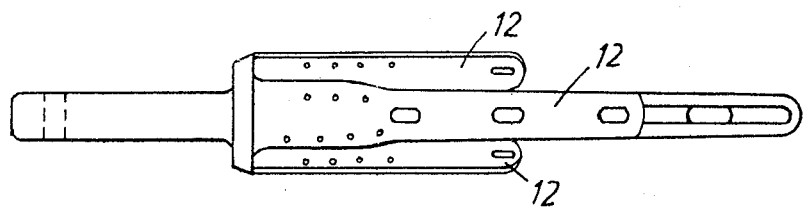
FIG. 10 is a side elevation of a mounting component.

The hip components are arranged for connection to the mounting components which are indicated by reference numerals 9 and 10. These mounting components have stems, indicated by reference numeral 11 and these stem diameters are, in the arrangement being described 14 mm and 16 mm, the stem length is 150 mm. The stems are of the Walldius type with three flanges, which are indicated by reference numeral 12 in FIG. 1. The precise construction of the mounting components is more clearly shown in FIG. 10 from which it will be seen that one of the flanges 12 is longer than the other two. The mounting component has a connection portion 13 which is in the form of a spigot.

The mounting component and the hip component may be made of any suitable material, for example Vitallium (Registered Trade Mark of Howmedica International Inc.).

Plastic sleeve 14 is a press fit over the spigot 13 so that it is effectively held against rotation. This sleeve 14 has a key way 15 and the outer dimensions are such that the hip component can be pushed over the mounting component spigot 13 and the key 8 will engage the key way 15 in the sleeve thus preventing rotation between the components.

As three hip components are provided of different sizes and two mounting components a hip resection system is thus provided which allows for two resection lengths, that is 120 mm, 160 mm and with two optional stem diameters. The parts can be assembled in the operating theatre to the required length and to fit the femur as required.

FIG. 2 shows a set of joint components, in this case femural knee components which can be used on a spherocentric knee. A set of tibial components which can be used with the femural knee components of FIG. 2 are shown in FIG. 3.

A knee resection system according to the invention can therefore comprise two or more mounting components of the kind shown in FIG. 1, complete with mounting sleeves 14, one or more femural knee components as shown in FIG. 2 and one or more tibial components as shown in FIG. 3.

Each of the femural components comprises a head 20 of known shape and which will not therefore be further described apart from stating that the portions which represent the condyles are made hollow and act as the engagement portion of the joint. This portion is connected to a connection part 21 which is again in the form of a hollow cylinder and of similar dimensions to the connection part 7 of the hip component shown in FIG. 1. A key 22 is again provided in each of the sockets 23 provided by the hollow cylinder and a raised ridge 24 is located adjacent the upper end of the connection portion. The use of this ridge 24 will be described later.

Each of the femural components is of a different size, in this embodiment 110 mm, 150 mm and 190 mm and they are arranged to be connected to the mounting components 9 and 10 of FIG. 1 by pushing them over the spigot 13 and locating the key 22 in the key way 15 of the sleeve 14. It will be appreciated that the mounting component is now used inverted but is still suitable for connection to the lower part of the femur.

The engagement portion of the femural component has an anatomical shaped patella flange, the sides are smooth and no sharp edges exist which might cause problems with soft tissue. As is mentioned above this component is made hollow to reduce weight.

The tibial component for use with the femural component is provided in three sizes, as shown in FIG. 3, a standard size 0 mm, 90 mm, 120 mm 150 mm. This component is again made from Vitallium and has a Walldius type stem 30 and two flanges 31. It will be seen that the 0 mm size does not have a stem of this type. The component has a platform with two bearing surfaces and is used to replace the head of the tibia, the bearing surfaces representing the lateral and medial condyles on the tibia and the shaped engagement portion on the femural component providing the lateral and medial condyles on the femur.

This knee resection system therefore provides three resection lengths of the femur and four resection lengths of the tibia along with stems of different diameter.

The femural component is assembled in the theatre to the required length and the coupling of the femural component and the tibial component uses the same procedure as with a spherocentric knee.

It will be appreciated that the invention can now provide a set of parts for an assembly which can be used to replace both of the joints associated with the femur of the patient and at the same time provides for the length of the components to be adjusted as required.

Due to the construction concerned it is possible to replace the joint components which carry the engagement portions without difficulty and this is advantageous if the patient is still growing.

Figure 4:
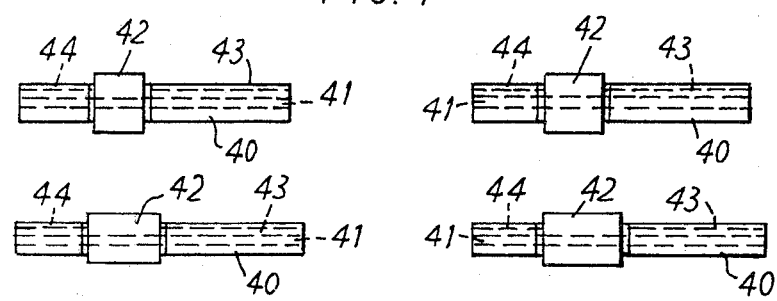
FIG. 4 is a diagrammatic representation of a set of mounting components which can be used with the parts shown in FIGS. 1 and 2.

FIG. 4 shows a set of alternative mounting components which can be used with the hip components shown in FIG. 1 and the femural knee components shown in FIG. 2. The mounting components shown in FIG. 4 each comprise a coupling shaft 40 which is made from a plastics material with a metal reinforcement rod 41 at its centre. Each of the shafts is circular and has a raised portion 42 which is of greater diameter than the remainder. Keyways 43 and 44 are provided on each side of the raised portion 42.

These mounting components can be used with the parts shown in FIGS. 1, 2 and 3 to provide a total femur system which comprises hip components 5, coupling shafts shown in FIG. 4, femural components as shown in FIG. 2 and tibial components as shown in FIG. 3.

The diameter of the coupling shaft 40 is such that it is a tight fit in the hip component 5 and the key 8 enters the appropriate keyway 44, the part of the shaft carrying the keyway 44 therefore acting as a connection part. The portion of the shaft carrying the keyway 43 also acts as a connection portion for the femural knee component 21 which is a push fit onto it with the key 22 engaging the keyway 43. The two joint components 15, 21 are pushed towards each other until their ends contact the raised portion 42.

In the particular arrangement being described the following lengths can be made with the components referred to:

| Hip Component (Length in mm) | Knee Component (Length in mm) | Shaft (Length in mm) | Length Total Femur (Length in mm) |
| --- | --- | --- | --- |
| 190 | 110 | 40 | 340 |
| 190 | 110 | 50 | 350 |
| 190 | 110 | 60 | 360 |
| 190 | 110 | 70 | 370 |
| 190 | 150 | 40 | 380 |
| 190 | 150 | 50 | 390 |
| 190 | 150 | 60 | 400 |
| 190 | 150 | 70 | 410 |
| 190 | 190 | 40 | 420 |
| 190 | 190 | 50 | 430 |
| 190 | 190 | 60 | 440 |
| 190 | 190 | 70 | 450 |

With this construction therefore the femur is totally replaced but with the set of parts described the surgeon can make up a suitable length of prosthesis to replace it.

Figure 7:
FIG. 7 is a diagrammatic representation of a washer for use with the spacers shown in FIGS. 5 and 6.
Figure 8:
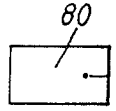
FIGS. 8 and 9 are diagrammatic front and end elevations of a retaining sleeve.
Figure 9:
Figure 12:
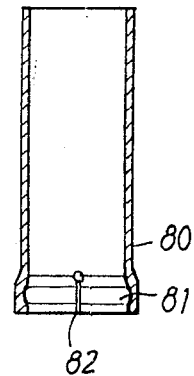
FIG. 12 is a cross-sectional side view of the retaining sleeve shown in FIGS. 8 and 9.

The last embodiment to be described is particularly suitable for growing patients and comprises an adjustable total femur system. In this case the same components as referred to in the example described above and with relation to FIG. 4 can be used with the addition of a set of split cylindrical spacers as shown in FIGS. 5 and 6, a washer FIG. 7 and a retaining sleeve as shown in FIGS. 8 and 9 and which is shown in more detail in FIG. 12.

Figure 5:
FIG. 5 is a diagrammatic representation of a set of spacers which can be used with one of the components shown in FIG. 4.
Figure 6:
FIG. 6 is an end view of the spacers shown in FIG. 5.
Figure 11:
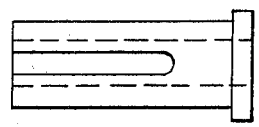
FIG. 11 is a side view of a sleeve for use with the component shown in FIG. 10.

The spacers as shown in FIGS. 5 and 6 are shown in six sizes ranging from 10 mm to 60 mm with steps of 10 mm. They can be placed around the portion of the shaft which carries the keyway 43 and kept in place by means of the retaining sleeve shown in FIGS. 8, 9 and 11 which slide over them. The plastic material washer of FIG. 7 is placed at the end of the spacers and the femural knee component is now pushed into place. One end of the retaining sleeve, 80, which is made from a plastics material is provided with an internal groove 81 and the end also carries four longitudinally extending slots 82. The sleeve can thus be snapped over the end of the femural knee component, the groove 81 being located on the ridge 24. This sleeve therefore holds the spacers in place and effectively alters the length between the joint components on the shaft.

As a number of shafts can be provided it will be appreciated that a vast variation can be achieved. With the arrangement being described the assembly can be used to achieve a maximum growth of 60 mm. The lengths which are achievable are equivalent to the ones shown in the Table but the following sizes can also be constructed, that is, 460, 470, 480, 490, 500 and 510 mm.

If a lengthening of the femur prosthesis is required due to growth, the following operation procedure can be employed:

The femur is placed in traction which must be enough to overcome muscle force and friction force in the push fit of the shaft and the femural knee component. After achieving the correct elongation an operation is performed. An incision half way on the femur is required to push up the retaining sleeve 80 and put in new spacers of the kind shown in FIG. 5. As the spacers are split it is possible to insert them from inside.

The retaining sleeve is again snap fitted around the femural component and the wound is closed. The effect is to lengthen the total prosthesis.

Although the invention has been described with regard to an assembly for use with a femur it could of course be used with other bones, the appropriate joint components being of suitable shape as required by the joint or joints concerned. The system allows for a prosthesis to be made up of modular parts which can be used to provide part of the joint, and/or parts of two or more joints provided the mounting component is suitable but the modular construction allows a single mounting component to employ joint components of different sizes and shapes, for example, as described in the arrangements set forth above. Again, the assembly can be used not only to replace a single joint but also replace a complete bone by providing the appropriate joint parts at each end.

We claim:

1. A modular prosthesis assembly for replacement of at least part of a joint and part of the length of a bone shaft comprising a mounting component provided with a connection portion and at least two joint components of similar shape but different dimensions and which can be connected alternatively to said mounting component, each of said joint components having an engagement portion and a connection part adapted for connection to said connection portion of said mounting component, the connection part of said two joint components being of different lengths, said different length connection parts each providing a different length for replacing by itself a part of the length of a natural bone shaft which can be connected to a remaining length of a natural bone shaft or artificial joint, and said mounting component and said at least two joint components thereby co-operating to effect selectively two prostheses of different bone shaft lengths.

2. A modular prosthesis assembly as claimed in claim 1 in which each of said similar joint components is in the form of a hip component having a head extending via a neck to said connection part.

3. A modular prosthesis assembly as claimed in claim 2 in which one of said heads and said necks of said similar joint components are of different sizes.

4. A modular prosthesis assembly as claimed in claim 1 in which each of said similar joint components is in the form of a femoral knee component each having an engagement portion to co-operate with a natural tibia or a tibia prosthesis component.

5. A modular prosthesis assembly as claimed in claim 4 including a tibia component adapted for alternative co-operation with said femoral knee components and having an attachment portion for attachment to a tibia.

6. A modular prosthesis assembly as claimed in claim 5 in which two or more tibia components of different dimensions are provided for alternative use with said femoral knee components.

7. A modular prosthesis assembly as claimed in claims 1, 2, 3, 4, 5, or 6 in which each of said mounting components has an attachment portion for attachment to a femur of the user.

8. A modular prosthesis assembly as claimed in claim 7 in which the attachment portion of said mounting component is adapted for attachment to either end of a femur.

9. A modular prosthesis assembly as claimed in claim 8 in which said attachment portion is in the form of a stem portion.

10. A modular prosthesis assembly as claimed in claim 9 in which said stem portion is of a Walldius type with three flanges for cementless fixation.

11. A modular prosthesis assembly as claimed in claim 7 in which said attachment portion is in the form of a stem portion.

12. A modular prosthesis assembly as claimed in claim 11 in which said stem portion is of the Walldius type with three flanges for cementless fixation.

13. A modular prosthesis assembly as claimed in any one of preceeding claims 1, 5 or 6 in which said mounting component has said connection portion and another connection portion at spaced apart ends, one connection portion being adapted for connection to a joint component in the form of a hip component having a head extending via a neck to said connection part, and the other connection portion being adapted for connection to a joint component in the form of a femoral knee component having an engagement portion to co-operate with a natural tibia or a tibia prosthesis component, and including two or more hip components and two or more femoral knee components for alternative use.

14. A modular prosthesis assembly as claimed in claim 13 in which said mounting components are in the form of a coupling shaft.

15. A modular prosthesis assembly as claimed in claim 14 in which means are provided for adjusting the distance between the joint components on the coupling shaft.

16. A modular prosthesis assembly as claimed in claim 1 in which the connection part of each joint component has a socket in which said connection portion of the co-operating mounting component can be located.

17. A modular prosthesis assembly as claimed in claim 16 in which said connection portion has a sleeve mounted on it which is keyed into said socket to prevent relative rotation between the components.

18. A modular prosthesis assembly as claimed in claim 17 in which said sleeve is made from a synthetic plastics material.

19. A modular prosthesis assembly as claimed in claim 18 in which said sleeve is a press fit into said connection portion.

20. A modular prosthesis assembly as claimed in claim 1 including a joint component of another different shape to said similar joint components, and providing part of a bone shaft and part of a joint which can co-operate with an appropriate part of a different natural or artificial joint to that with which the joint components of similar shape are intended to co-operate.

21. A modular prosthesis assembly as claimed in claims 1 and 20 in which said mounting component has connection portions at spaced apart ends, for connection to one of the similar joint components at one end and connection to another joint component of different shape at the other end to provide a bone replacement prosthesis.

22. The modular prosthesis assembly as defined in claim 1 wherein each of said two joint components is defined by an integral homogeneous one-piece head and connection part, and each connection part is a generally elongated shaft.

23. The modular prosthesis assembly as defined in claim 25 wherein each of said elongated shafts and said mounting component connection portion include relatively telescopically engageable means for telescopically connecting said elongated shafts and said mounting component connection portion.

24. The modular prosthesis assembly as defined in claim 23 including means for selectively variably adjusting the relative telescopic position between each of said elongated shafts and said mounting component connection portion.

25. The modular prosthesis assembly as defined in claim 25 wherein each of said head and connection parts are joined by a neck offset from its associated elongated shaft.

* * * * *